United States Patent [19]

Forsythe, Jr. et al.

[11] 4,190,530
[45] Feb. 26, 1980

[54] CENTRIFUGAL METHOD AND APPARATUS FOR PROCESSING FLUID MATERIALS

[75] Inventors: Jesse G. Forsythe, Jr., Media, Pa.; Donald R. Johnson, Wilmington; Linda M. St. Onge, Newark, both of Del.

[73] Assignee: E. I. Du Pont de Nemours and Company, Wilmington, Del.

[21] Appl. No.: 892,508

[22] Filed: Apr. 3, 1978

[51] Int. Cl.² ............................................. B01D 15/06
[52] U.S. Cl. .................................... 210/31 R; 210/78; 210/144; 210/267; 210/378; 210/512; 233/14 R
[58] Field of Search ............... 210/31 R, 78, 144, 267, 210/360, 378, 512; 233/1 D, 12, 14 R, 26, 46; 162/384

[56] References Cited

U.S. PATENT DOCUMENTS

| | | | |
|---|---|---|---|
| 3,567,029 | 3/1971 | Quame | 210/249 |
| 3,722,789 | 3/1973 | Kennedy | 233/26 |
| 3,810,545 | 5/1974 | Filz et al. | 210/360 X |
| 3,877,634 | 4/1975 | Rohde | 233/14 R |
| 3,951,334 | 4/1976 | Fleming et al. | 233/26 |
| 3,953,172 | 4/1976 | Shapiro et al. | 23/230 B |

Primary Examiner—Charles N. Hart
Assistant Examiner—Ferris H. Lander

[57] ABSTRACT

Samples to be analyzed, such as physiological fluids (blood, urine, etc.) may be processed using centrifugal techniques. The sample is centrifugally passed through a separation column to extract the desired component from the aqueous phase. Next, the extracted component is washed free of extraneous materials and then eluted from the separating column by centrifugally passing a suitable solvent therethrough. The aqueous phase and extracted components are collected in separate containers.

To facilitate this method, an apparatus is provided that accommodates switching between fluid flow paths in a centrifuge. The centrifuge utilizes a swinging bucket rotor which contains a separating column, the top end of which employs a fluid reservoir for holding the sample to be extracted. Fluids are passed through the separating column (a first flow path) from a central distributor in the centrifuge rotor while in operation. An outer ring of swinging buckets holds two receptacles (the second and third flow paths), one for the aqueous phase and one for the solvent phase containing the sample extract or physiological component. These two receptacles are placed in radial fluidic alignment with the separating column by the technique of reversing the direction of rotation of the rotor, thus switching between two fluid flow paths.

31 Claims, 13 Drawing Figures

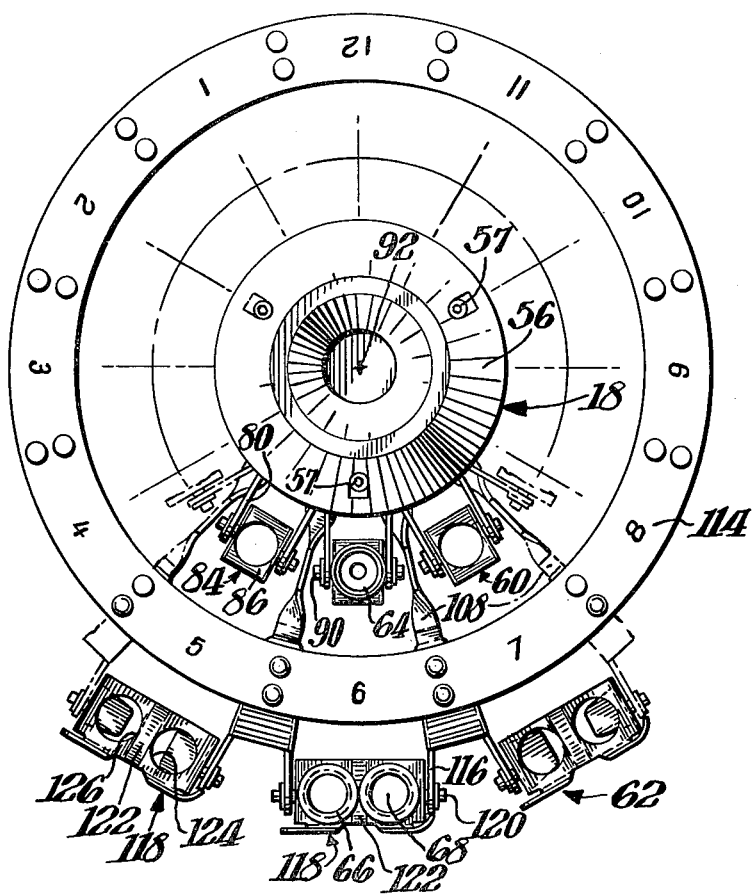
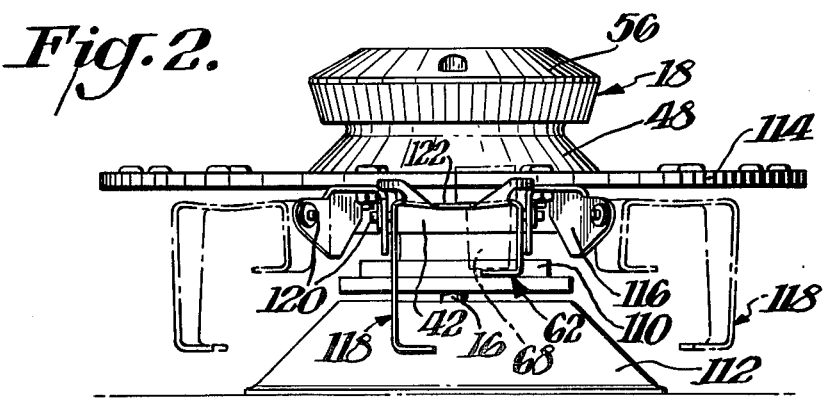

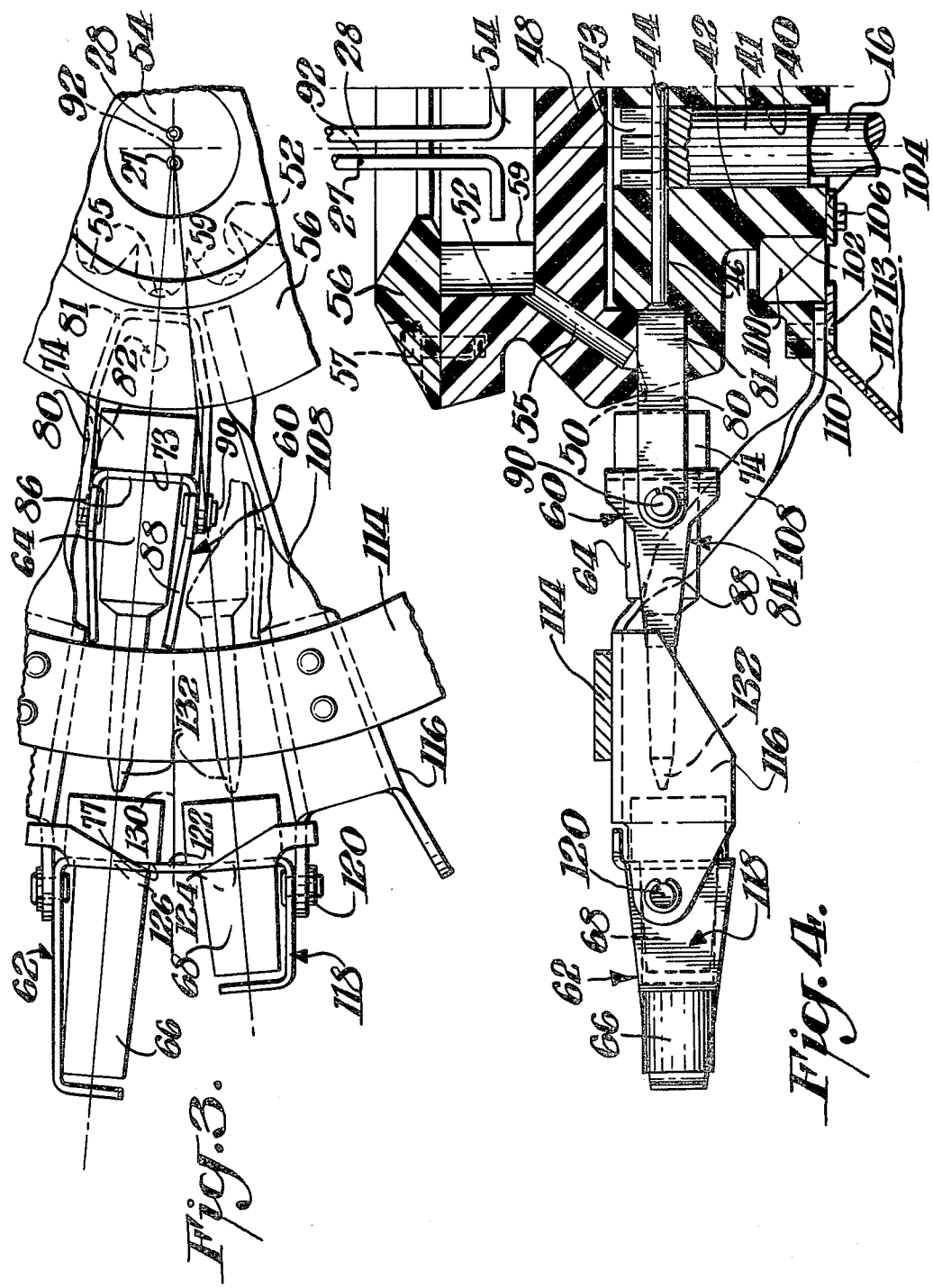

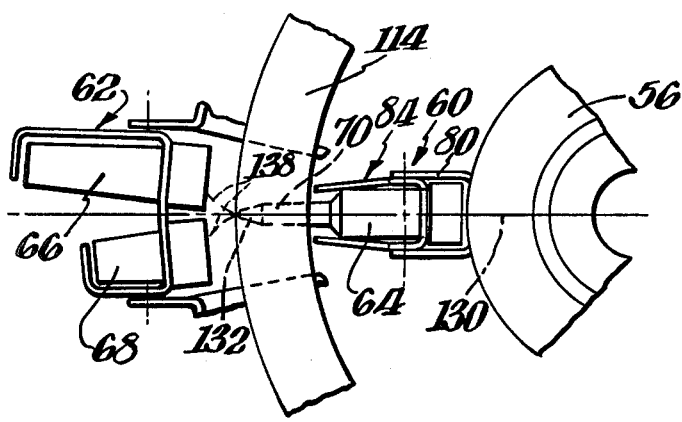
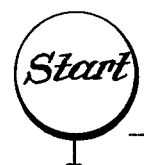
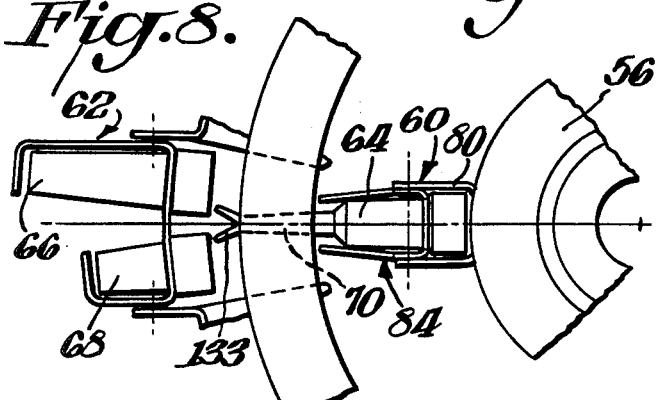
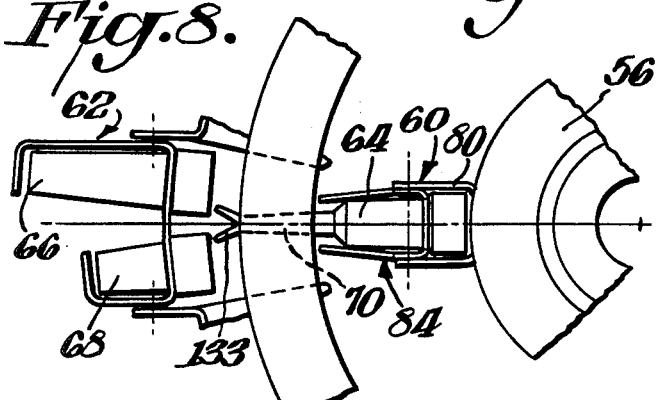
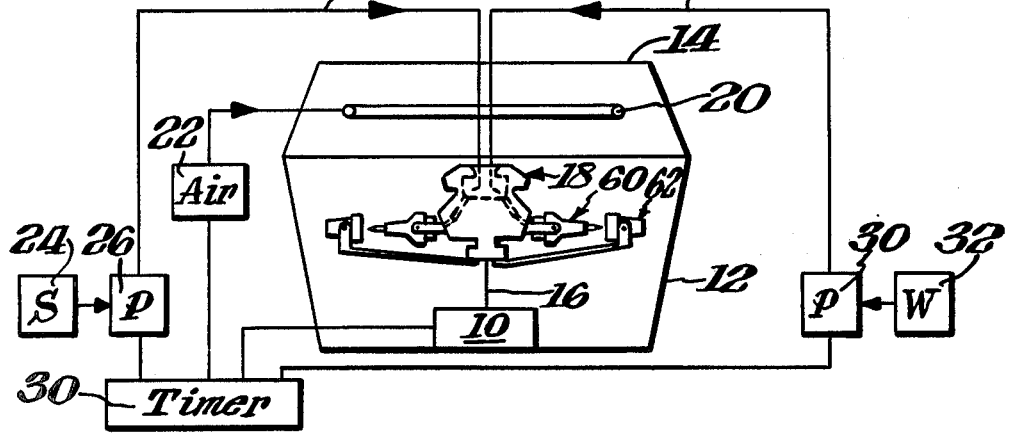

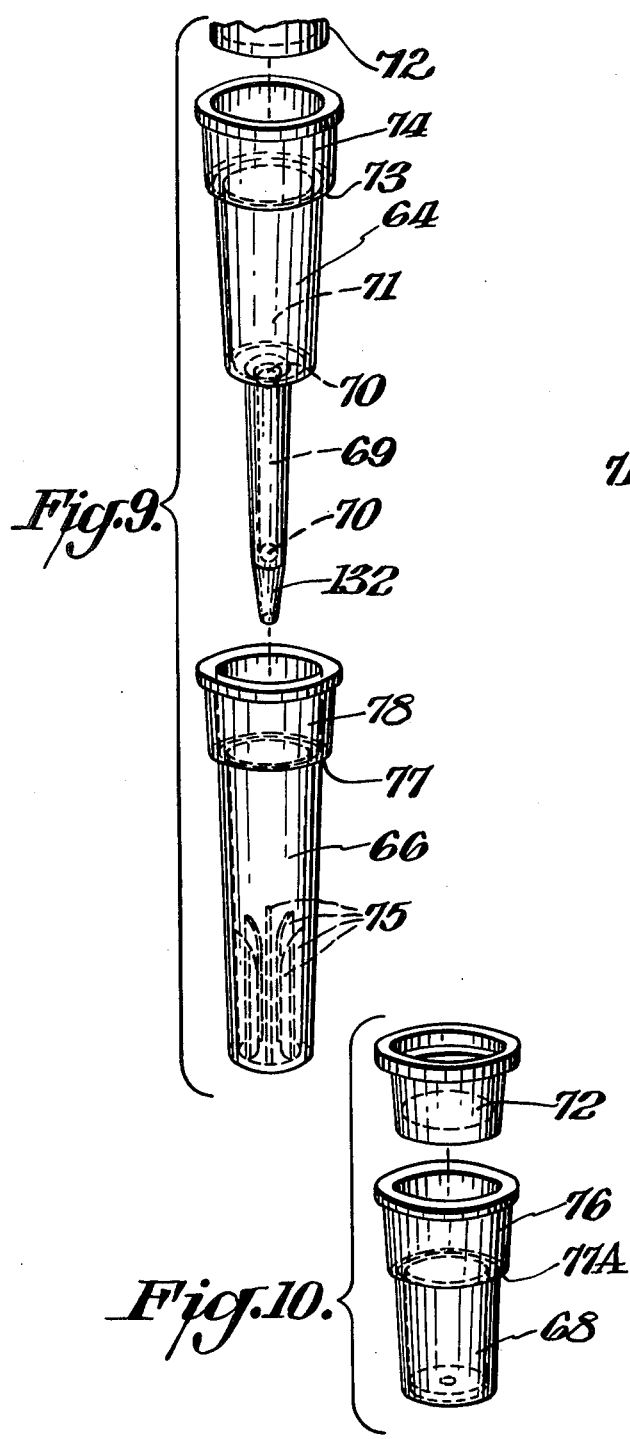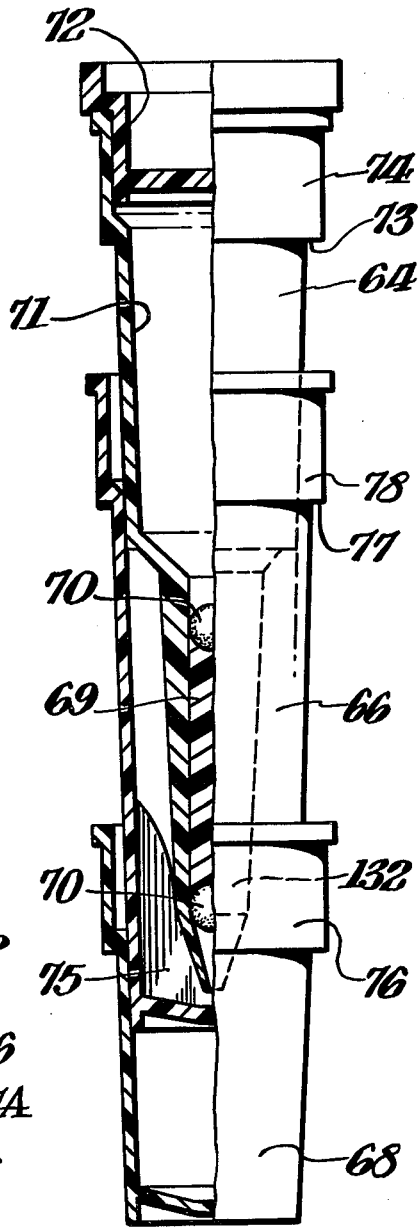

CENTRIFUGAL METHOD AND APPARATUS FOR PROCESSING FLUID MATERIALS

DESCRIPTION

TECHNICAL FIELD

This invention relates to processing fluid materials and, more particularly, to a method and apparatus for fluid switching.

BACKGROUND ART

The processing of fluids can occur in many different fields for many different applications. It is often necessary or desirable in the processing of fluids to switch from one flow path to another. It is also often necessary or desirable in the processing of fluids to utilize centrifugal force as the mechanism for enhancing the fluid flow. For example, one may wish to filter fluids to determine different components or constituents of a sample, to separate fluids, to concentrate fluids, and the like. In each of these applications, the fluids often must be passed through different separating media, filters or dividers. Also, sufficient driving force must be provided to attain the flow rates desired.

In one application, for example, the analysis of samples, particularly biological samples, i.e., physiological fluids such as whole blood, serum or urine, one must separate or extract the desired components from the sample. Analytical procedures that typically require this step include trace organic and inorganic analyses for environmental control in such areas as monitoring industrial effluents, pesticide run-off and drinking water; impurity and formulation analyses in the food and pharmaceutical industries and process monitoring in many industrial operations. Typically, these analyses require that the extraction or separation step be performed manually. Once the extraction is made, the extracted or separated components of the desired material can be analyzed by any known technique such as thin-layer chromatography, liquid chromatography, gas chromatography, and the like.

One such extraction technique is described by Quame in U.S. Pat. No. 3,567,029. Quame describes the use of a disposable separating column filled with a particular solid phase, capable of extracting certain lipophilic compounds, including the most commonly encountered abused drugs, such as phenobarbital, amphetamine, methadone and the like, In a typical drug extraction, such as from a urine sample, Quame allows the urine sample to pass through the column. The column selectively adsorbs any lipophilic drugs contained in the urine, thereby extracting the lipophilic drugs from the aqueous phase. Next, the adsorbed drugs are eluted from the column by a solvent and any residual aqueous phase is retained by a filter. This technique worked quite well for some urine samples. Unfortunately, however, it is somewhat time consuming because it is manual and because the sample and the solvent phases slowly pass through the column and filter combination.

Another technique for assaying fluids is that described by Shapiro et al. in U.S. Pat. No. 3,953,172. Shapiro uses a swinging bucket centrifuge rotor with the buckets each holding a separating column. The fluid samples to be assayed are mixed with a reagent at the central part of the centrifuge rotor and then allowed to pass, under the influence of centrifugal force, through the single separating column. While Shapiro does have the advantage of using centrifugal force to speed up the process, it is still limited somewhat in application, in that multiple solvents cannot readily be used. It is therefore difficult to recover materials adsorbed on the column. It is difficult to concentrate the desired materials for later analyses. No fluid switching is provided, i.e., no means is provided to permit different fluids flowing through a separating column to pass to different collecting vessels. Conceivably, this might be accomplished by various valving arrangements, but such becomes relatively complex and, in any event, apparently has never been accomplished.

It is therefore an object of this invention to provide an improved method for processing fluid materials.

Another object of this invention is to provide an improved apparatus for processing fluid materials.

DISCLOSURE OF INVENTION

According to one aspect of the invention, fluid materials are processed, using first, second, and third unconnected fluid flow paths, by placing said materials in said first fluid flow path, using centrifugal force, by rotating all of said paths about a common axis in a first sense to move said materials along said first flow path to one of said second and third flow paths, and switching said materials from said first path to the other one of said second and third flow paths by angularly accelerating said first flow path about said axis at a rate different from the angular acceleration of said second and third flow paths. In one embodiment switching is accomplished by effecting the net angular acceleration of the first flow path relative to said second and third flow paths in a sense opposite said first sense.

In either of these cases, the fluid discharging from the first flow path is radially directed outwardly to one of the second and third flow paths. By varying the relative angular accelerations, the fluid from the first path is redirected to the other of the second and third flow paths. The fluid from the first flow path may be in substantially direct radial alignment with one of the other two flow paths or it may follow an involute path. In either case, the relative angular positions of the flow paths are varied to facilitate fluid switching. The flow paths may include filters, separating columns, etc. In some applications the switching step may be accomplished without permitting rotation of the first flow path relative to the second and third flow paths.

According to another aspect of the invention, material is extracted from a fluid sample by centrifugally passing the sample through a separation means to extract the material from the sample fluid. Next, the extracted material is eluted by centrifugally passing a solvent for the material through the separation means, and finally the solvent and dissolved materials are collected. The extracted material may be concentrated by evaporating the solvent.

The first flow path may contain a separating column filled with particles of a cross-linked styrene-divinylbenzene copolymer, and the fluid materials may be passed through the first flow path to the second flow path using an aqueous phase, leaving the lipophilic portions of the fluid materials on the column. Interstital residues of the aqueous phase are removed from the column by the centrifugal force. A solvent for the lipophilic materials on the column may be introduced to the first flow path to transfer the lipophilic materials to the third flow path.

The invention also includes an apparatus for processing fluid materials using a swinging bucket centrifuge which includes a rotor, a first plurality of tubular devices disposed circumferentially about said rotor, each forming a first fluid flow path, pivotally mounted on the rotor, a source of processing fluids, a distributor incorporated into the rotor for directing the processing fluids radially outward into the first tubular devices, a second plurality of pairs of tubular devices disposed circumferentially about said rotor, each forming a second fluid flow path, pivotally and rotatably mounted on the rotor radially outside of the first plurality of tubular devices, a drive for selectively accelerating the rotor in a first sense and a second sense different than said first sense to cause said devices to swing outwardly and upwardly to establish a disconnected fluid flow path from said distributor through corresponding ones of said first devices and corresponding ones of said pairs of said second devices according to the sense of acceleration of the rotor. In one embodiment of the invention, the second sense is such as to reverse the direction of rotation of the rotor. In another, the direction of rotation may remain the same and a detent used to allow the angular position of the second plurality of devices to change relative to that of the first plurality of devices.

In accordance with one aspect of the invention, the second plurality of devices is rotatably mounted on the rotor hub to permit limited rotational movement between the rotor hub and the second devices between a first position, in which the fluid flow paths of the first devices are in radial alignment with corresponding fluid flow paths of one of each of the pairs of second devices when the rotor is accelerated in the first sense, and a second position in which the fluid flow paths of the first devices are in radial alignment with corresponding fluid flow paths of the other of each of said pairs of the second devices when the rotor is accelerated in said second sense. In another aspect of the invention, the fluid from the first flow path follows an involute path to the second flow path. In another aspect of the invention, starved flow through a Y conduit in each first flow path is switched from one arm of the Y to the other by reversing the sense of acceleration or rotation of the first devices. The pairs of second flow paths are in radial alignment with the respective arms of the Y to complete the switched flow paths.

The first tubular device may be a chromatographic separating column and the second tubular devices each a receptacle. The first and second devices may all be tapered to permit their nesting into a stacked array, which results in the formation of an effective vapor barrier seal for the columns during storage. This reduces evaporation of the contents of the pretreated separating column and facilitates the integrity of column prior to use.

BRIEF DESCRIPTION OF THE DRAWINGS

FIG. 1 is a plan view of a swinging bucket centrifuge rotor, constructed in accordance with a preferred embodiment of this invention, for processing fluid materials;

FIG. 2 is a side elevation view of the rotor illustrated in FIG. 1;

FIG. 3 is a partial plan view of the swinging bucket rotor of FIG. 1 illustrated in an operating condition;

FIG. 4 is a partial sectional elevation view of the swinging bucket rotor of FIG. 1 illustrated in an operating condition;

FIG. 5 is a block representation of a method of this invention for extracting samples of materials from fluids;

FIG. 6 is a block-schematic diagram of a centrifuge system incorporating the swinging bucket rotor of FIG. 1 for effecting the method FIG. 5;

FIG. 7 is a partial plan view of an alternative rotor configuration that may be used in the method of this invention and for processing fluid materials;

FIG. 8 is a partial plan view of another alternative rotor configuration that may be used for processing fluid materials;

FIGS. 9-11 are illustrations of a nested separating column and receptacle that may be used in the swinging bucket rotor of FIG. 1.

DETAILED DESCRIPTION OF THE PREFERRED EMBODIMENT

Figure 12:
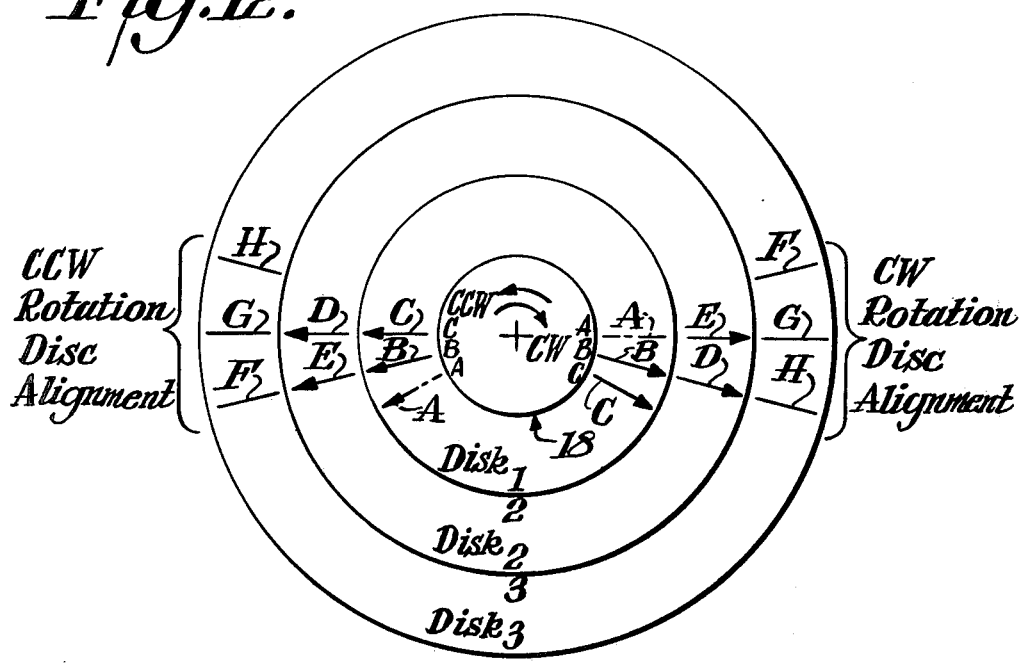
FIGS. 12 and 13 are respective plane and elevation views of an alternative rotor configuration that may be used to effect fluid switching.

According to this invention, fluid materials may be processed by first placing the fluid materials in a first flow path. This flow path may be a filter, a separating column, or other device which affects the fluid materials physically or chemically. The materials are forced through the first flow path with the aid of centrifugal force to reduce processing time. Upon exiting from the first fluid flow path, the processed fluid materials may be switched so as to pass to either a second or a third fluid flow path. The second and third fluid flow paths may be any of the devices mentioned above and, in addition, may be simple receptacles. The flow paths, being disconnected, may be switched to pass the materials from the first flow path to either the second or third flow paths by angularly accelerating the first flow path about a centrifuge axis at a rate that is different than the angular acceleration of the second and third flow paths. The first flow path may be the one that is accelerated or decelerated. Conversely, the second and third flow paths, which operate together, may be the ones that are angularly accelerated or decelerated relative to the first flow path. By angularly accelerating the first flow path on the one hand and the second and third flow paths on the other hand at different angular rates either in the same sense or in opposite senses, the first flow path is caused to change its angular position such that fluid exiting from it may switch from either the second fluid flow path to the third or from the third fluid flow path to the second, as the case may be.

In particular applications, the first fluid flow path may be positioned circumferentially in between the second and third flow paths and the involute flow path from the exit of the first flow path used to effect the switching. In this instance, the direction of rotation of both the respective first flow path on the one hand and the second and third flow paths on the other, are reversed, i.e., the acceleration is reversed, to effect the fluidic switching. In another application, the first flow path is allowed to move angularly from the second to the third flow path while both are rotating in the same sense, i.e., the acceleration is different. In still another, the first flow path is allowed to be move angularly from the third to the second by reversal of the rotational sense of the first path with respect to the second and third flow paths.

The ability to effect fluidic switching while centrifuging the flow paths has many applications. For example, there is illustrated in FIG. 5 a functional block diagram describing the various steps of the method of this invention by which a physiological fluid sample may be processed to extract a desired material therefrom. This extraction method utilizes a centrifuge with fluid switching capabilities. To begin the method, an extraction cartridge 64, illustrated in FIGS. 9-11, is separated from its nested stack and placed in a centrifuge rotor, in an orientation, as will be described hereinafter, so that centrifugal force provides the bead necessary to force fluids through the column. The extraction column is positioned radially inside of a circumferentially positioned first cup 66 and a second cup 68. The centrifuge rotor that will be described has a capability of switching the fluid flow path from the exit of the extraction column such that the effluent from the extraction column may be passed by choice either to the first cup 66 or to the second cup 68.

The rotor used is a swinging bucket rotor. Hence, as the rotor turns, say in a first sense, such as a clockwise direction, the tip of the extraction column is radially aligned with the first cup. The centrifugal force acting on the horizontal (radially disposed) column forces the sample through the resin bed at a controlled flow rate. The materials to be extracted from the sample are retained by the resin while other materials pass through the column and are collected in the first cup. Next, a predetermined volume of wash solvent or reagent is delivered to the fluid distribution hub of the rotor. The wash is divided into equal aliquots and directed to the resin beds in the extraction columns and collected in the first cups.

In this step the wash removes unadsorbed sample components from the resin bed. In the next step, rotational speed is increased so that the resulting increased centrifugal force passes residual wash to the first cup. The direction of rotor rotation is changed to shift the tip of the extraction column into radial alignment with the second cup. Eluting solvent is dispensed from a solvent reservoir and aliquoted to the several column positions. The solvent passes through the column under the influence of centrifugal force, extracting the adsorbed materials which are eluted from the resin bed of the column and collected in the second cup. The rotor is now slowed, and jets of (heated) air are directed to the second cup from an annular ring appropriately located. The eluted solvent is evaporated, leaving a dry residue of the extracted materials in the second cup. Hence, simply by reversing the rotor rotational sense the fluid paths are changed and material extraction and recovery achieved.

The apparatus of this invention which facilitates this fluid switching as is required to implement the method described, is best seen in FIG. 6 which is a partial block, partial schematic diagram of an otherwise conventional centrifuge modified in accordance with this invention. The centrifuge includes a drive motor 10 mounted in a protective housing 12 having a lid 14. The motor 10 is adapted to drive, through an appropriate drive mechanism 16, the rotor 18 of this invention. In the upper portion of the housing 12 there is provided a tubular ring 20 which is connected to a source of gas 22 which provides downwardly directed jets of drying gas to quickly evaporate any solvent retained in the second cups, as will be described. The drying gas may be heated and may be air, N₂ or other suitable gases. Similarly, introduced through the top of the cover 14, are lines connecting from a solvent reservoir 24 through a suitable pump or valve 26 to provide solvent to the distributor of the rotor 18. This distributor described generally so far, may be the type described by Rohde et al. in U.S. Pat. No. 3,877,634. Also included is a second line 28 which is connected from a pump or valve 30 which supplies water or other solvent from a second reservoir 32. Additional solvent lines may be introduced as desired. The pumps or valves 26 and 30, as well as the air supply 22, are selectively actuated by electrical signals derived from a timer 30. The timer also controls the operational direction and speed of the motor 10.

Although this invention has been described in conjunction with the use of what is designated in FIG. 6 as a timer 30, it is to be understood that this timer may be any suitable timer that is known in the art. This may include a simple stepping switch or it may include something more sophisticated such as a microprocessor working with a programmable read only memory such as is available on integrated circuit chips and are available from Fairchild and designated F8.

The details of the rotor, which forms the heart of this invention, may be best understood with reference to FIG. 1-4. The rotor is formed of several parts. The drive shaft 16 is connected to a conventional gyro-type drive 41 (FIG. 4) for a centrifuge rotor. The drive enters a drive bore 40 formed in a mounting hub 42. The hub itself may be formed of a suitable material such as stainless steel, Delrin ® plastic or aluminum. The gyro drive 41, which may have the usual radial slots 43, is adapted to engage a vertical load support and drive key 44 which is housed in a diametrical bore 46 formed in the hub 42.

Secured to the upper part of the hub is a distributor 48 whose function is to divide and direct fluids radially outward through small nozzles 50 and to support swinging buckets, as will be described. The distributor, which may be formed of the same material as the hub, has plural compartments 52, one for each nozzle 50, with inwardly radially extending vanes 59 which serve as flow dividers for each compartment. In this manner, a fluid which is directed into the distributor by one of the lines 27 or 28 and directed radially outward is divided by the rotation of the distributor into equal segments. Each compartment 52 is connected by a suitable bore 55 to its respective nozzle. An annular cap 56, which may be formed of the same material as the hub and the distributor, is secured to the top of the distributor as by screws 57. The distributor is similarly secured to the hub. Its hollow interior is simply to close compartments 52.

The remainder of the rotor includes an inner set 60 and an outer set 62 of swinging buckets. The inner set of buckets 60 is adapted to support the first fluid flow path such as the extraction column 64, whereas the outer set of buckets are in pairs and are adapted to support, respectively, the second fluid flow path, here depicted as cup 66 and the third fluid flow path, here depicted as a second cup 68. As may be seen from FIGS. 9-11, the extraction or separating column includes a resin bed 69 as will be described hereinafter. Each end of the resin bed is secured by means of a porous plug 70 to permit the passage of fluids therethrough and yet prevent the particles comprising the resin bed from becoming dislodged from position. The plugs 70 are somewhat larger than the inner diameter of the tube in which the resin bed is contained. The upper portion 71 of the extraction column 64 is enlarged and tapered to provide a fluid reservoir whereas the very top portion 74 is enlarged still further to accommodate the introduction of a cap or plug 72. The lower end of the extraction column is in the shape of a nozzle 132 to direct effluent fluids outwardly in a small diameter stream to one of the first and second cups in accordance with the fluid switching of this invention.

The first cup 66 is also a tapered unit, the interior bottom portion of which has inwardly directed flanges 75 to maintain the lower end of the extraction column 64 properly positioned when they are nested prior to use. The first cup itself is tapered with the upper portion 78 enlarged to accommodate the cap 72. Finally, the second cup 68 is also tapered with an enlarged upper portion 76 to accommodate the cap 72. The extraction column, first cup and second cup are all constructed to be roughly the same upper diameter such that, with their taper, they may be stacked in a nested array as depicted in FIG. 11. For storage, this nested array facilitates vapor sealing and maintains the extraction column moist during storage if required.

The inner swinging buckets 60 are hung from a U-shaped bracket 80 which is secured in radially configured slots 81 formed in the lower portion of the distributor 48. In this manner, when the distributor is secured as by screws 82 to the hub, the hub retains the brackets in position. The brackets 80 also contain a second U-shaped piece or bucket 84, the inner portion 86 of the U having a hole formed to accommodate the extraction column. The extreme upper portion of the extraction column forms a shoulder 73 which is adapted to engage the hole. The uprights of the bracket 84 extend outwardly to intercept positioning brackets 108 of the outer assembly with rotation in either direction, thus driving the outer assembly and positioning inner assembly and hence, the nozzle tip 132 relative to the cup 66, 68. The lower portion of the uprights 88 of the U-shaped bracket 84 are secured as by pivot pins 90 to the ends of the U-shaped fixed mounting bracket 80. This permits the inner bucket assembly 60 to swing outwardly and upwardly when the rotor is spun about the axis 92 such that, in in operation, the extraction column is generally horizontal and extending radially outward.

Under these conditions, centrifugal force moves fluids, applied from the distributor nozzles 50, through the column at a low radial velocity. Likewise, any samples introduced into the reservoir 71 of the extraction column 64, are moved outwardly through the columns. Upon passing through the column and leaving the nozzle tip 132, the fluids are switched to either the first cup or the second cup 67.

The cups 66, 68 are pivotally suspended by the outer swinging buckets This is accomplished by the utilization of a bearing 100 which is secured to the outside lower portion of the hub 42 in an annular recess 102 and retained at the lower end by a bearing retainer ring 104 secured as by bolts 106 to the hub 42. Radial, vertical positioning brackets 108 are secured at their lower end to an annular bearing clamp 110, which grips the outer portion of the bearing 100 between the bearing clamp 110 and a ring stand 112. The gripping is accomplished by bolts 113. The brackets 108 extend upwardly to and are connected at their outer end to a support ring 114. The outer ends 116 of the bracket 108 are U-shaped and adjacent brackets are secured by a pivot 120 to a U-shaped outer bucket 118. These outer buckets 118 have a cross member 122 with a pair of holes 124, 126. Each bucket 118 is at a radial position corresponding nominally to the center of the circumferential position of each nozzle 50, the bucket having the two adjacent mounting holes 124 and 126 formed therein to receive, respectively, the first cup 66 and the second cup 68. Both cups are retained therein by their shoulders 77 and 77A, respectively.

The configuration of the positioning brackets 108 is such that they permit limited rotation of the outer buckets 62 relative to the inner buckets 60. The limited rotation is such that either the first cups 66 or the second cups 68 may be positioned in radial alignment with the nozzle 132 and hence with the extraction column 64. It is noted that the extraction column as well as the first cups and second cups each form a fluid flow path which may be placed into or out of alignment to effect fluid switching therebetween. It is also noted that each of these columns and cups or flow paths, as the case may be, are not in contact but connected together, but are physically separated radially from each other, even when in the spinning, horizontal position. The fluid switching hence may be obtained by rotating the rotor in the clockwise sense if it is desired to switch to, i.e., align the column with, the first cup 66, or, if it is desired to switch the fluid flow from the column to the second cup 68, the direction of spin is reversed, i.e., the acceleration is reversed, and the rotor is driven in a counterclockwise direction allowing inner buckets to shift in angular position relative to the outer buckets such that the column and second cup are now in alignment. All of the parts forming the various brackets, etc. may be formed of a suitable material having adequate structural strength such as stainless steel.

Stated more broadly, to effect fluid switching from the first fluid flow paths (the columns 64) to one or the other of the second fluid flow paths, the first or second cups 66, 68, it is merely necessary to change the acceleration of the hub 42, supporting the columns 64, relative to that of the bearing mounted support ring which positions, rotationally, the first and second cups radially outside of the columns 64. Alternatively, of course, the drive shaft 16 could drive the support ring with its outer fluid flow paths (cups 66, 68) with the distributor hub bearing mounted.

For the sake of clarity, the use of the apparatus of this invention may be described in the general context of one of its applications, namely, the extraction and concentration of drugs (lipophilic materials) from serum or other body fluids. According to this method, the fluids are first buffered to a desired pH depending on drug type. In this example, the drugs or lipophilic materials are then extracted from the aqueous phase of the serum by passing the solution centrifugally over a finely divided porous resin. This is followed by an aqueous rinse. Waste passes to the first cup. Excess aqueous phase is removed from the resin by increasing the speed of the rotor. Following this, the direction of spin is reversed and lipophilic components are eluted from the resin bed with an appropriate organic solvent. The solvent may then be removed from the second cup by evaporation to leave a dried lipophilic material residue for quantitative analysis using high pressure liquid chromatographic techniques.

Various materials may be used for the separating column. These are for the most part known, but by way of example, include the ion exchange resins which may be used for the sorption of organic and inorganic ions typically for trace impurity removal, i.e., aminoacid, sugar, protein and peptide analysis. These ion exchange resins include anion, cation and mixed bed. A preferred resin, although not an ion exchange resin, is a high cross-linked styrene-divinylbenzene copolymer sold commercially under the tradename "Amberlite" designated XAD-2.

Other column materials that may also be used are gel permeation, which include porous polyacrylamide beads, activated charcoal, agarose gel beads, polystyrene beads and coated glass beads. These columns may be used for the resolution of compounds of differing molecular weights. Another column material is that used for affinity chromatography and includes agarose supports, polyacrylamide supports and polystyrene supports to which a specific compound has been bonded to permit selected chemical reactions on the columns and supports to which a particular compound, enzymes, or antibody has been bonded. Other column packing materials for specific separations are wellknown in the art and need not be mentioned here. Suffice it to say, that whatever the column material selected it should be particulate sized appropriately to prevent fluid flow therethrough under normal gravity conditions but yet to accommodate the desired radial fluid flow under the centrifugal force that is applied to the column. One particular size that has been used successfully in this regard is particles of the "Amberlite" XAD-2 resin sized in the 40 to 100 micron range with the centrifuge spun at 1000 rpm with the columns located at an average radial distance of 11 cm from the spin axis. Other resins and materials may require different sizings.

Some extraction columns will contain a filter in the reservoir for the purpose of trapping solid, particulate or fibrous materials that may be present in the sample, i.e., fibrin in plasma samples, or amorphous materials in urine samples. The filter protects the porous plug and column. The filter may be loose and porous such as glass wool, cotton, polyester fiber, or may be solid particles such as glass beads, or even nylon and the like. Glass beads are preferred.

FIG. 7 in an alternative embodiment of the invention is depicted. In this embodiment, the outer buckets 62 may be keyed to the inner buckets 60 as by a suitable pin or by the removal of the bearing 100, such that they are locked in position. The nozzle 50 and the column 64 of the first fluid flow path have their axes in alignment with the very middle, denoted by the reference numeral 130, or mid-position between the first cup 66 and the second cup 68. Under these conditions, the exit nozzle 132 of the extraction column 64 is disposed at a small radial distance away from the second and third fluid flow paths (cups 64, 66). Thus, when the radial fluid velocity is relatively small compared to the tangential velocity of the rotating nozzle 132 of the extraction column 64, the fluid path in free flight, superimposed on the rotor is that of an involute curve 135 having as its base circle the locus of the nozzle tip as it spins about the rotor spin axis. The superimposed path is independent of rotor speed for practical purposes. Consequently, the symmetrical disposition of the second and first cup permit the use of this involute path by rotating the rotor in a clockwise or counterclockwise direction for the fluidic switching of the fluid stream passing outwardly from the nozzle to a corresponding one or the other of the first cup or second cup. The fluid path leaving the nozzle tip trails the direction of rotation. Thus, in this alternative embodiment of the invention the rotational direction would be reversed for the flow path selection to the first cup or second cup as herein previously described.

In FIG. 8 another alternative of the embodiment of the invention is illustrated. In this embodiment, the nozzle 132 of the extraction column 64 may be fitted with a Y connector 133 radially disposed outward with the stem of the Y facing the axis of the rotation and the two arms facing outward with one arm in the disection and the other arm opposite the disection of rotation. The alignment of the flow paths is the same as described in connection with the embodiment depicted in FIG. 7, i.e., the outer buckets 62 and locked to the inner buckets 60. If now the flow rate of fluid through the extraction column is limited such that the passage does not fill the channels in the Y, i.e., starved flow, the fluids flowing through the Y connector will always be along the trailing wall of the connector with respect to the direction of rotation. Thus, by simply reversing the direction of rotation of the rotor, the fluid path may be directed to one arm of the Y or the other. This again achieves the desired fluidic switching by reverse rotation, i.e., acceleration, within the concept of this invention.

A further alternative embodiment, although not shown, it to use detents that may be actuated by a solenoid or other appropriate mechanism to maintain the circumferential column position in alignment with the back (in an angular sense) cup. By releasing the detent, the inner buckets will move forward to the next detent position at which the column is in alignment with the forward cup.

Figure 13:
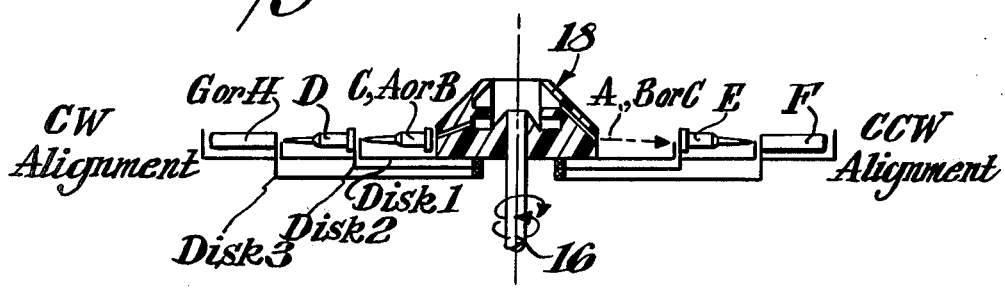

The centrifugal switching concept of this invention may be expanded to that illustrated in FIGS. 12 and 13 to include a third set of swinging buckets which may be positioned on the outside of the outer swinging buckets 62 depicted in FIGS. 1–4. This is illustrated schematically and may be implemented as shown in FIGS. 12 and 13 with the addition of one more bearing positioned separately but below the bearing 100 of FIG. 4 such that both of the outer sets of swinging buckets may be independently rotatable relative to the rotor. Again, their rotation is limited to permit them only the option of shifting upon the direction of the spin one position to either side of their normal position. Under these conditions, as seen in the schematic illustration, the several annular sets of swinging buckets will be described in simple terms as disc 1, disc 2 and disc 3.

Thus, under the conditions of clockwise rotation, it may be seen that flow paths B, D and H are in alignment. If, however, the direction of rotation is reversed to counterclockwise, disc 2 and disc 3 each shift one position so that the flow path is now B, E, F. This provides more variation in the switching combinations that are available. Still other combinations of flow paths may be obtained by driving different disc elements.

There has thus been described a relatively simple method and apparatus for fluid flow switching. As switching is accomplished rotationally, it provides high speed and great versatility in applying different solvents and materials to the different flow paths. Each flow path acts on the fluid flowing therethrough in a different manner. The described rotor operating in a programmed centrifuge greatly facilitates extraction of various biological materials from residence within a physiological fluid.

We claim:

1. A centrifuge apparatus for processing fluid materials and the like comprising:
   a rotor,

11 a first plurality of tubular devices disposed circumferentially about said rotor, each forming first fluid flow paths, a source of processing fluids, a distributor in said rotor for directing said processing fluids radially outward through said first fluid flow paths, a second plurality of pairs of tubular devices disposed circumferentially about said rotor, each forming a second fluid flow path, radially outside of said first plurality of tubular devices, a drive for selectively accelerating said rotor in a first sense and a second sense different than said first sense to cause said tubular devices to establish disconnected fluid flow paths from said distributor through corresponding ones of said first devices and corresponding ones of said pairs of second devices according to the sense of acceleration of said rotor.

2. The apparatus of claim 1 wherein said centrifuge is a swinging bucket centrifuge and said tubular devices are pivotally mounted on said rotor.

3. The apparatus of claim 2 which also includes a third plurality of pairs of devices pivotally mounted on said rotor, radially outside of said second plurality of devices, each third tubular device forming a fluid flow path, whereby said rotor rotation also causes said third devices to swing outwardly and upwardly to continue said disconnected fluid flow path from said distributor.

4. The apparatus of claim 3 wherein said second sense is opposite said first sense and said third plurality of buckets are rotatably mounted on said rotor to permit limited rotational movement between said second devices and said third devices between a first position in which the fluid flow path of one of said pairs of said second devices is in radial alignment with corresponding fluid flow paths of one of each of said pairs of third devices when said rotor is rotated in said first sense and a second position in which the fluid flow paths of each said second device is in radial alignment with corresponding fluid flow paths of the other of each of said pairs of said third devices when said rotor is rotated in said second sense.

5. The apparatus of claim 2 wherein said drive is reversible and said second sense is opposite said first sense.

6. The apparatus of claim 5 wherein said first tubular device contains a separating column and said second tubular devices are receptacles.

7. The apparatus of claim 6 wherein said separating column is filled with a resin.

8. The apparatus of claim 7 wherein said resin is particles of a cross-linked styrene-divinyl benzene copolymer.

9. The apparatus of claim 6 wherein said copolymer particles are sized sufficiently small such that aqueous solutions will not pass through said column under the influence of gravity alone.

10. The apparatus of claim 9 wherein said first device and said second pair of devices are each tapered to permit nesting in a stacked array, thereby to reduce evaporation of the contents of said first device.

11. The apparatus of claim 10 wherein each said first fluid flow device has an exit end, and a Y-shaped tube connected thereto with the arms of the Y leading and trailing said exit end and having an inside cross-sectional area greater than twice the cross-sectional area of said exit end.

12. The apparatus of claim 5 wherein said first device and each of said second pair of devices are tapered to permit nesting in a stacked array, thereby to reduce evaporation of the contents of said first device.

13. The apparatus of claim 5 wherein said rotatable mounting includes supports for said second buckets which are contacted by said first buckets to rotate said second buckets.

14. The apparatus of claim 5 wherein said first devices each are circumferentially fixedly positioned in between each pair of said second devices, whereby fluid from said first device follows an involute path to meet said second devices.

15. The apparatus of claim 14 wherein said first tubular device contains a separating column and said second tubular devices are receptacles.

16. The apparatus of claim 5 wherein said second plurality of devices is rotatably mounted on said rotor to permit limited rotational movement between said rotor and said second devices between a first position in which the fluid flow paths of said first devices are in radial alignment with corresponding fluid flow paths of one of each of said pairs of second devices when said rotor is rotated in said first sense and a second position in which the fluid flow paths of said first devices are in radial alignment with corresponding fluid flow paths of the other of each of said pairs of second devices when said rotor is rotated in said secon sense.

17. The apparatus of claim 16 wherein said rotatable mounting includes supports for said second devices which are contacted by said first devices to rotate said second devices.

18. The apparatus of claim 16 wherein said first tubular device contains a separating column and said second tubular devices are receptacles.

19. The apparatus of claim 18 wherein said separating column is filled with one or more of the group of particulate materials consisting of resins, silicas, silicates, alumina, aluminates and charcoal.

20. The apparatus of claim 19 wherein said resin in particles of a cross-linked styrene-divinyl benzene copolymer.

21. The apparatus of claim 20 wherein said copolymer particles are sized sufficiently small such that aqueous solutions will not pass through said column under the influence of gravity alone.

22. The apparatus of claim 21 wherein said first device and said second pair of devices are each tapered to permit nesting in a stacked array, thereby to reduce evaporation of the contents of said first device.

23. A centrifugal method of processing fluid materials using first, second, and third unconnected fluid flow paths comprising the steps of:

placing said materials in said first fluid flow path, using centrifugal force, by rotating all of said paths about a common axis in a first sense, to move said materials along said first flow path to one of said second and third flow paths, and switching said materials from said first flow path to the other one of said second and third flow paths by angularly accelerating said first flow path differently than said second and third flow paths about said axis.

24. The method of claim 23 wherein said net angular acceleration of said first flow path relative to said second and third flow paths is in a sense opposite said first sense.

25. The method of claim 23 wherein said swtiching step is accomplished by permitting limited rotation of said first flow path relative to said second and third flow paths upon reversal of said acceleration sense to achieve radial alignment of said first flow path with one of said second and third flow paths.

26. The method of claim 23 wherein said materials in said first flow path are passed through a separating column.

27. The method of claim 26 wherein said column is filled with particles of a cross-linked styrene-divinyl benzene copolymer and said method includes the steps of:
   introducing said materials to said column and to said second flow path using an aqueous phase thereby immobilizing lipophilic portions of said materials on said column,
   introducing a solvent for lipophilic materials to said column and to said third flow path to collect said lipophilic materials.

28. A method of extracting a material from a first liquid phase comprising the steps of:
   centrifugally passing the first liquid phase through a separating means to extract said material from the first liquid phase,
   eluting said extracted material by centrifugally passing a solvent for said material through said separating means, and
   collecting only the eluted solvent entrained material.

29. The method of claim 28 which includes the additional step of evaporating said solvent by spinning said collected solvent entrained material in a centrifuge.

30. The method of claim 29 wherein air is directed against said solvent entrained material while spinning.

31. A centrifuge apparatus for processing fluid materials and the like comprising:
   a rotor,
   a first plurality of tubular devices disposed circumferentially about said rotor, each forming first fluid flow paths,
   a source of processing fluids,
   a distributor in said rotor for directing said processing fluids radially outward through said first fluid flow paths,
   a second plurality of pairs of tubular devices disposed circumferentially about said rotor, each forming a second fluid flow path, radially outside of said first plurality of tubular devices,
   a drive for said rotor for subjecting said fluid flow paths to centrifugal force to establish disconnected fluid flow paths from said distributor through corresponding ones of said first devices and a corresponding one of said pairs of second devices, and
   means for switching the angular position of said first and second flow paths such that said flow paths of said first devices communicate with corresponding others of said pairs of said second devices.

* * * * *